United States Patent [19]
Kovac

[11] Patent Number: 6,039,686
[45] Date of Patent: Mar. 21, 2000

[54] SYSTEM AND A METHOD FOR THE LONG TERM CURE OF RECURRENT URINARY FEMALE INCONTINENCE

[76] Inventor: S. Robert Kovac, 411 Stonehaven, Kettering, Ohio 45429

[21] Appl. No.: 09/111,525

[22] Filed: Jul. 8, 1998

Related U.S. Application Data

[63] Continuation-in-part of application No. 08/820,053, Mar. 18, 1997, abandoned.

[51] Int. Cl.$^7$ ........................................ A61B 19/00
[52] U.S. Cl. ................................................ 600/30
[58] Field of Search ..................... 600/29, 30; 128/897, 128/898, 885–887, DIG. 25; 606/232, 65, 67, 72, 73, 75; 623/12.16

[56] References Cited

U.S. PATENT DOCUMENTS

| | | |
|---|---|---|
| 3,580,313 | 5/1971 | McKnight . |
| 4,632,100 | 12/1986 | Somers et al. . |
| 4,920,986 | 5/1990 | Biswas . |
| 5,007,894 | 4/1991 | Enhorning . |
| 5,012,822 | 5/1991 | Schwarz . |
| 5,013,292 | 5/1991 | Lemay . |
| 5,036,867 | 8/1991 | Biswas . |
| 5,123,428 | 6/1992 | Schwarz . |
| 5,256,133 | 10/1993 | Spitz . |
| 5,362,294 | 11/1994 | Seitzinger . |
| 5,386,836 | 2/1995 | Biswas . |
| 5,439,467 | 8/1995 | Benderev et al. ...................... 606/139 |
| 5,520,700 | 5/1996 | Bayer et al. ............................ 606/139 |
| 5,562,689 | 10/1996 | Green et al. . |
| 5,611,515 | 3/1997 | Benderev et al. . |

OTHER PUBLICATIONS

Scheuer, Steven, "The Modified Pereyra Bladder Neck Suspension Procedure Using Mitek Gll Anchors". Dec. 1993.

Mascio, "Therapy of Urinary Stress Incontinence in Women". Apr. 1993.

Raz, Shlomo et al, The Raz Bladder Neck Suspension: Results In 206 Pateints, The Journal Of Urology, pp. 845–850, Sep. 1992.

Klutke, Carl, "The Anatomy of Stress Incontinence: Magnetic Resonance Imaging of The Female Bladder Neck and Urethra", the Journal of Urology, vol. 143, Mar. 1990; pp. 563–566.

Waxman, Steve, Advanced Urologic Surgery for Urinary Incontinence:, The Female Patient, vol. 21, Mar. 1996; pp. 93–100.

Zimmern, Philippe E., "Four–Corner Bladder Neck Suspension", Atlas of the Urologic Clinics of North America, vol. 2, No. 1, Apr. 1994; pp. 29–36.

Gilja, Ivan, "A Modified Raz Bladder Neck Suspension Operation (Transvaginal Burch)", The Journal of Urology, vol. 153, May 1995; pp. 1455–1457.

Pereyra, Armand J., "Pubourethral Supports in Perspective: Modified Pereyra Procedure for Urinary Incontinence", Instruments & Methods, vol. 59, No. 5, May 1982; pp. 643–648.

(List continued on next page.)

*Primary Examiner*—Samuel Gilbert
*Attorney, Agent, or Firm*—Polster, Lieder, Woodruff & Lucchesi, L.C.

[57] ABSTRACT

A pubic bone-mounted urethra stabilization and support system and method therefor for the long term cure of recurrent female urinary incontinence. The system comprises, a pair of anchors affixed to the posterior/inferior pubic bone, sutures attach to the anchors and a mesh sling passing behind and about the urethra and the adjacent endopelvic fascia and having ends attached to the anchors by the anchor-mounted sutures. The method includes the steps of accessing said urethra with the endopelvic fascia therebehind and the pubic bone, properly locating and attaching the anchors to the pubic bone, properly locating the sling about the urethra and adjacent endopubic fascia and suturing and tensioning the ends of the sling to the anchors, causing said sling to restore, support and stabilize functional urethral continence anatomy and prevent urethral descent under intraabdominal pressure.

34 Claims, 12 Drawing Sheets

OTHER PUBLICATIONS

Benderev, Theodore V., "Anchor Fixation and Other Modifications of Endoscopic Bladder Neck Suspension", Urology, vol. 40, No. 5, Nov. 1992; pp. 409–418.

Burch, John C., "Urethrovaginal Fixation to Copper's Ligament for Correction of Stress Incontinence, Cystocele, and Prolapse", Am. J. Obst. & Gynec, vol. 81, No. 2, Feb. 1961: pp. 281–290.

Beck, R. Peter, "Treatment of Urinary Stress Incontinence With Anterior Colporrhaphy", Journal of the American College of Obstetricians and Gynecologists, vol. 59, No. 3, Mar. 1982; pp. 267–274.

Benderev, Theodore V., "A Modified Percutaneous Outpatient Bladder Neck Suspension System", Journal of Urology, vol. 152, Dec. 1994; pp. 2316–2320.

Brochure— "Vesica® Percutaneous Bladder Neck Stabilization Kit", Microvasive Boston Scientific Corporation, 1995.

Ulmsten, U., "An Ambulatory Surgical Procedure Under Local Anesthesia for Treatment of Female Urinary Incontinence", International Urogynecology Journal, 1996; pp. 81–86.

Kovac, S. Robert et al., "Pubic Bone Suburethral Stabilization Sling for Recurrent Urinary Incontinence", *Obstetrics & Gynecology*, vol. 89, No. 4, Apr. 1997, pp. 624–627.

Kovac, S. Robert et al., "Pubic bone suburethral stabilizing sling: a long–term cure for SUI?", *Contemporary OB/GYN*, Feb., 1998, pp. 52–76.

To be Published: Kovac, S. Robert, "Follow–up of the pubic bone suburethal stabilization sling operation for recurrent urinary incontinence", *Journal of Pelvic Surgery*.

Marshall, Victor Fray et al., "The Correction of Stress Incontinence By Simple Vesicourethral Suspension", *Surgery, Tynecology and Obstetrics*, 1949; 88:, pp. 509–518.

Klutke, John James et al, "Transvaginal Bladder Neck Suspension To Cooper's Ligament: A Modified Pereyra Procedure", Obstetrics & Gynecology, vol. 88, No. 2, Aug. 1996, pp. 294–296.

Leach, Gary E., "Bone Fixation Technique For Transvaginal Needle Suspension", Urology, vol. XXXI, No. 5, May 1988, pp. 388–390.

Winter, Chester C., "Peripubic Urethropexy For Urinary Stress Incontinence In Women", Urology, vol. XX, No. 4, Oct. 1982, pp. 408–411.

Kovac, S. Robert, "Follow–up Of The Pubic Bone Suburethral Stabilization Sling Operation For Recurrent Urinary Incontinence (Kovac Procedure)", Journal of Pelvic Surgery, May 1999, pp. 156–160.

Leach, Gary E. et al, "Female Stress Urinary Incontinence Clinical Guidelines Panel Summary Report On Surgical Management Of Female Stress Urinary Incontinence", American Urological Association, vol. 158, Sep. 1997, pp. 158–880.

Horbach, Nicollette S., et al "A Suburethral Sling Procedure With Polytetrafluoroethylene For The Treatment Of Genuine Stress Incontinence In Patients With Low Urethral Closure Pressure", Obstetrics & Gynecology, vol. 71, No. 4, Apr. 1998, pp. 648–652.

Morgan, J.E. et al, "The Marlex Sling Operation For The Treatment Of Recurrent Stress Urinary Incontinence: A 16–Year Review", Am. J. Obstet. Gynecol, vol. 151 No. 2, Jan. 15, 1985, pp. 224–227.

Das, Sakti et al, "Laparoscopic Colpo–Suspension", The Journal of Urology, vol. 154, pp. 1119–1121.

Holschneider, C.H., et al., "The Modified Pereyra Procedure In Recurrent Stress Urinary Incontinence: A 15–Year Review", Obstetrics & Gynecology, vol. 83, No. 4, Apr. 1994, pp. 5 73–578.

Stamey, Thomas A., "Endoscopic Suspension Of The Vesical Neck For Urinary Incontinence In Females" Ann. Surg., vol. 2, No. 4, Oct. 1980, pp. 465–471.

SYSTEM AND A METHOD FOR THE LONG TERM CURE OF RECURRENT URINARY FEMALE INCONTINENCE

REFERENCE TO RELATED APPLICATION

This is a continuation-in-part of application Ser. No. 08/820,053, filed Mar. 18, 1997 now abandoned, in the name of S. Robert Kovac, entitled A SYSTEM AND A METHOD FOR THE LONG TERM CURE OF RECURRENT URINARY FEMALE INCONTINENCE.

TECHNICAL FIELD

The invention relates to a system and method for the effective long-term cure of recurrent female urinary incontinence, and more particularly to a urethra stabilization and support system attached to the posterior/inferior pubic bone and a method for accomplishing this in which the urethra is positioned in the anatomically proper position.

BACKGROUND ART

The problem of recurrent female urinary incontinence, or the inability to control urination, is a major and debilitating one affecting millions of women in the United States alone. One particular type that frequently occurs in women is stress urinary incontinence, which is precipitated by coughing, straining, or heavy lifting. Mild cases may be treated by exercises involving tightening and relaxing of the perineal and gluteal muscles or by sympathomimetic drug therapy. Severe cases, however, may require surgery to correct the underlying anatomic defect. It is this surgical correction which is the subject of the present invention.

In general, continence is considered to be a function of urethral support and coaptation. For coaptation to successfully prevent or cure incontinence, the urethra must be supported and stabilized in its normal anatomic position. The female's natural support system for the urethra is a hammock-like supportive layer composed of endopelvic fascia, the anterior vaginal wall, and a distal attachment to the pubic bone. Weakening and elongation of the pubourethral ligaments and the arcus tendineus fascia pelvis, weakening of the endopelvic fascia and pubourethral prolapse of the anterior vaginal wall, and their complex interaction with intraabdominal forces are all suspected to play a role in the loss of pelvic support for the urethra and subsequent hypermobility to an unnaturally low non-anatomic position, leading to urinary incontinence.

Many procedures have been devised to treat urinary incontinence with the goal of elevating the neck of the bladder to return it to a higher retropubic position. Some involve the creation of a compensatory pubovaginal sling through a variety of needle suspension procedures; others employ a suburethral mesh to act as a compensatory suburethral sling to avoid the possibility that the sutures used in the needles suspension procedures will easily tear.

Many of the needle suspension procedures involve placing sutures in the endopelvic fascia or the anterior vaginal wall on either side of the urethra and attaching them to fixation sites such as bone and soft tissue. Alternatively, the sutures are attached to artificial anchors placed within the pelvis, at the superior border of the pubis, or rectus abdominus fascia. A major problem with this type of procedure is that the very fascial and muscular support structures that are sutured for support are often stretched, damaged, or otherwise deficient to begin with, and remain so after the procedure. It is therefore difficult to employ them successfully as reinforcements for surgical repair.

The pubovaginal sling procedure, in which a mesh is placed under the urethra to provide elevation and support of the urethra and bladder neck, has enjoyed an excellent surgical success rate. It is generally preferable for more complicated cases of recurrent genuine stress urinary incontinence, particularly in patients who have failed prior surgery, who are obese, or whose lifestyles involve heavy lifting and accompanying increased intraabdominal pressure. However, problems with voiding disfunction and urinary retention, detrusor instability, and infection and erosion of sling materials that can lead to urethrovesical and vesicovaginal fistulas are cause for concern. Additionally, this procedure is more technically challenging, presents greater blood loss, longer operative time, and a prolonged postoperative recovery.

These techniques use a variety of attachment sites for bladder neck and urethral support, such as the superior portion of the pubis, Cooper's ligament, or rectus abdominus fascia. This results in placement of the urethra in an unnaturally high position with respect to its normal anatomical retropubic position so that problems with voiding and urinary retention frequently arise after the procedure. Further, this abnormal positioning of the urethra in conjunction with failure of the supporting tissues and poor surgical technique have often led to a recurrence of incontinence since all of these operations create a compensatory abnormality rather than restoring the normal anatomy.

A related difficulty that contributes to the unnatural positioning of the urethra is that some attachment sites, such as the rectus abdominus fascia, require very long sutures and accompanying difficulty in achieving the proper tension in the sutures. This can result in increased lateral movement and momentum of the support structures or mesh sling when they are moved due to intraabdominal pressures.

The present invention addresses and corrects these and other difficulties by affecting the continence mechanism directly and providing a predictable and lasting permanent cure for the problem of recurrent female urinary incontinence.

It has been found that the key site for control of continence has not been heretofore addressed. It has further been found that the urethral hypermobility observed in most incontinent patients is caused by a lax or torn arcus tendineus facia pelvis attachment at its origin near the anterior levator arch in the immediate retropubic position at the site of the pubourethral ligaments. Repair and reinforcement of this area to stabilize the urethra in its normal position may be equally important as repair of the endopelvic facia. Therefore, the key site for control of continence is the paraurethral attachments of the pubourethral ligaments to the sides of the urethra at the intermediate 60% of the urethral length. This is simulated through the employment of a mesh sling system which supports this site and restores the bladder neck and urethra to their normal anatomic retropubic position. Additionally, when placed in this position, the lateral sides of the mesh serve to act as pubourethral ligaments which help to prevent undue descent of the urethra.

It has also been found that although the superior portion of the pubic bone is a functional and secure fixation site for incontinence repair, a key to restoring the urethra to its normal anatomical position is using the posterior/inferior border of the pubic bone, not the superior portion, as the attachment sites for the mesh sling system. Proper tensioning of the mesh sling system is made easier by using this portion of the pubic bone as the attachment site, due in part to the fact that shorter sutures and an innovative mesh suturing pattern is used. This serves to avoid the problems heretofore discussed associated with an improperly high retropubic positioning of the urethra.

DISCLOSURE OF THE INVENTION

According to the invention there is provided a pubic bone-mounted urethra stabilization and support system and a method for the long term cure of recurrent female urinary incontinence.

The system comprises a pair of anchors affixed to the posterior/inferior pubic bone, sutures attached to the anchors, and a mesh sling passing behind and about the urethra and the adjacent endopelvic fascia and having ends attached to the anchors by the anchor-mounted sutures. In particular, a pair of anchor screws are located on either side of the symphysis pubis in the retropubic area posteriorly and at about 0.5 cm superiorly of the inferior edge of the ischial ramus. Sutures connect the anchor screws to the mesh sling. The mesh sling directly supports the urethra by its placement on the endopelvic fascia in the area of the intermediate 60 percent portion of the urethra as will be later described in greater detail.

The method includes the steps of accessing said urethra and pubic bone, properly locating and attaching the anchors to the pubic bone, properly locating the sling about the urethra and suturing and tensioning the ends of the sling to the anchors, causing said sling to restore, support and stabilize functional urethral continence anatomy and prevent urethral descent under intraabdominal pressure.

To access the urethra and pubic bone, a pair of divergent incisions are made, beginning at the posterior urethral fold, in the anterior vaginal wall. This creates a triangular flap to expose the operative field. Care must be taken to separate the anterior vaginal wall from the adjoining endopelvic fascia to leave the endopelvic fascia intact. Direct visualization and palpation is next employed to evaluate the integrity of the lateral attachment of the endopelvic fascia to each arcus tendineus fascia pelvis, repairing any damage by suturing if necessary.

The pubic bone is next located by palpation. The course of the arcus from the ischial spine to the arcus insertion into the posterior/inferior aspect of the pubic bone is palpated to locate the proper site for the anchor screws, which is at either side of the symphysis pubis in the retropubic area posteriorly and at about 0.5 cm superiorly of the inferior edge of the ischial ramus. An anchor screw, which is provided with a pair of permanent sutures, is driven into the pubic bone at this location and set. An identical anchor screw is then driven into a symmetrically located position on the other side of the symphysis pubis.

A sling, comprised of a substantially rectangular patch of surgical mesh, is next laid upon the endopelvic fascia such that its longitudinal edges extend transversely of the urethra which is below the endopelvic fascia. Four permanent sutures are used to transfix the mesh along the lateral borders of the urethra at the edges of the mesh. These sutures are so positioned as to create a slight trough-like space between the mesh and the endopelvic fascia and urethra This space prevents undue tension on the urethra by the mesh when the mesh is formed into a sling. The permanent sutures of the anchor screws are then woven transversely of the mesh in opposite directions between the longitudinal edges of the mesh and inset from the transverse mesh edges. These sutures are then bilaterally tied with appropriate tensioning to transform the mesh into a sling.

Finally, any additional necessary repairs, including the sequential tying of the repair sutures for attaching the endopelvic fascia to the arcus tendineus fascia pelvis, are made. The cut edges of the anterior vaginal wall are approximated with sutures, and the cul-de-sac and posterior vaginal segment defects are repaired.

DETAILED DESCRIPTION OF THE INVENTION

Figure 1:
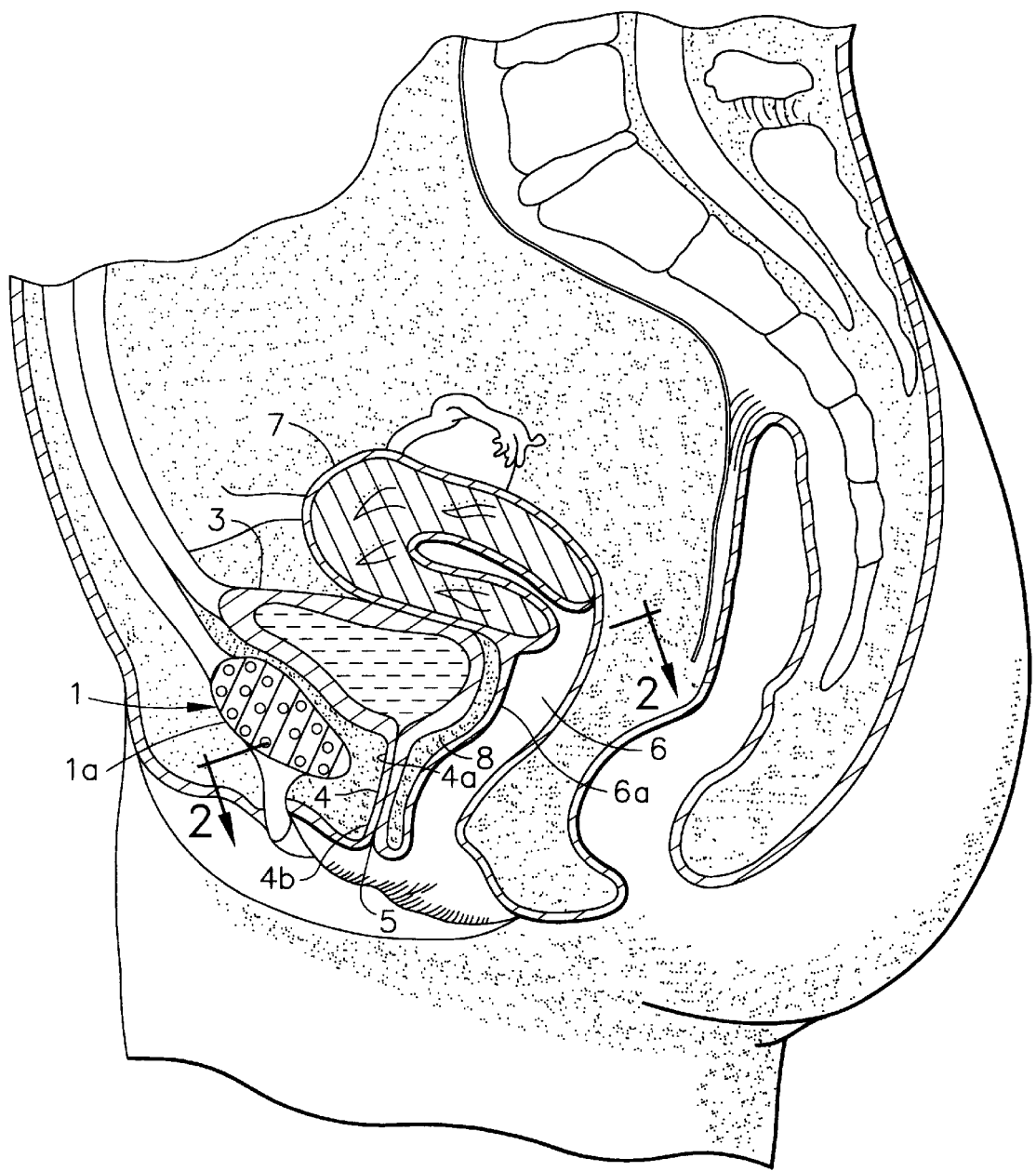
FIG. 1 is a fragmentary midsagittal cross-sectional view of the pelvic region illustrating the disposition of the urethra, bladder and vagina together with neighboring organs in a healthy woman.
Figure 2:
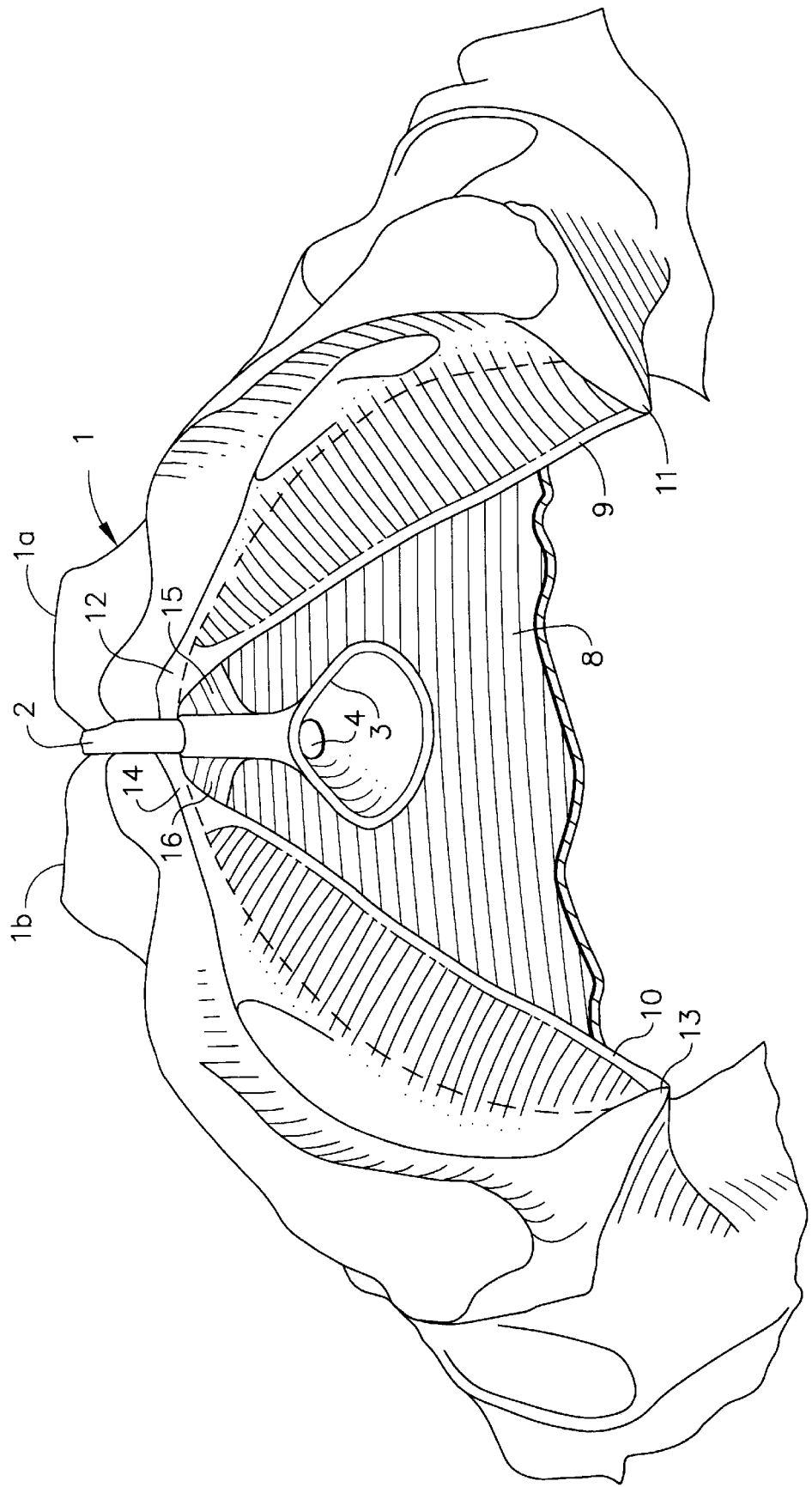
FIG. 2 is a fragmentary transverse view generally as seen along the line 2—2 of FIG. 1, illustrating the pubic bone, the bladder, the urethra, the arcus tendineus fascia, the endopelvic fascia and the pubourethral ligaments.
Figure 3:
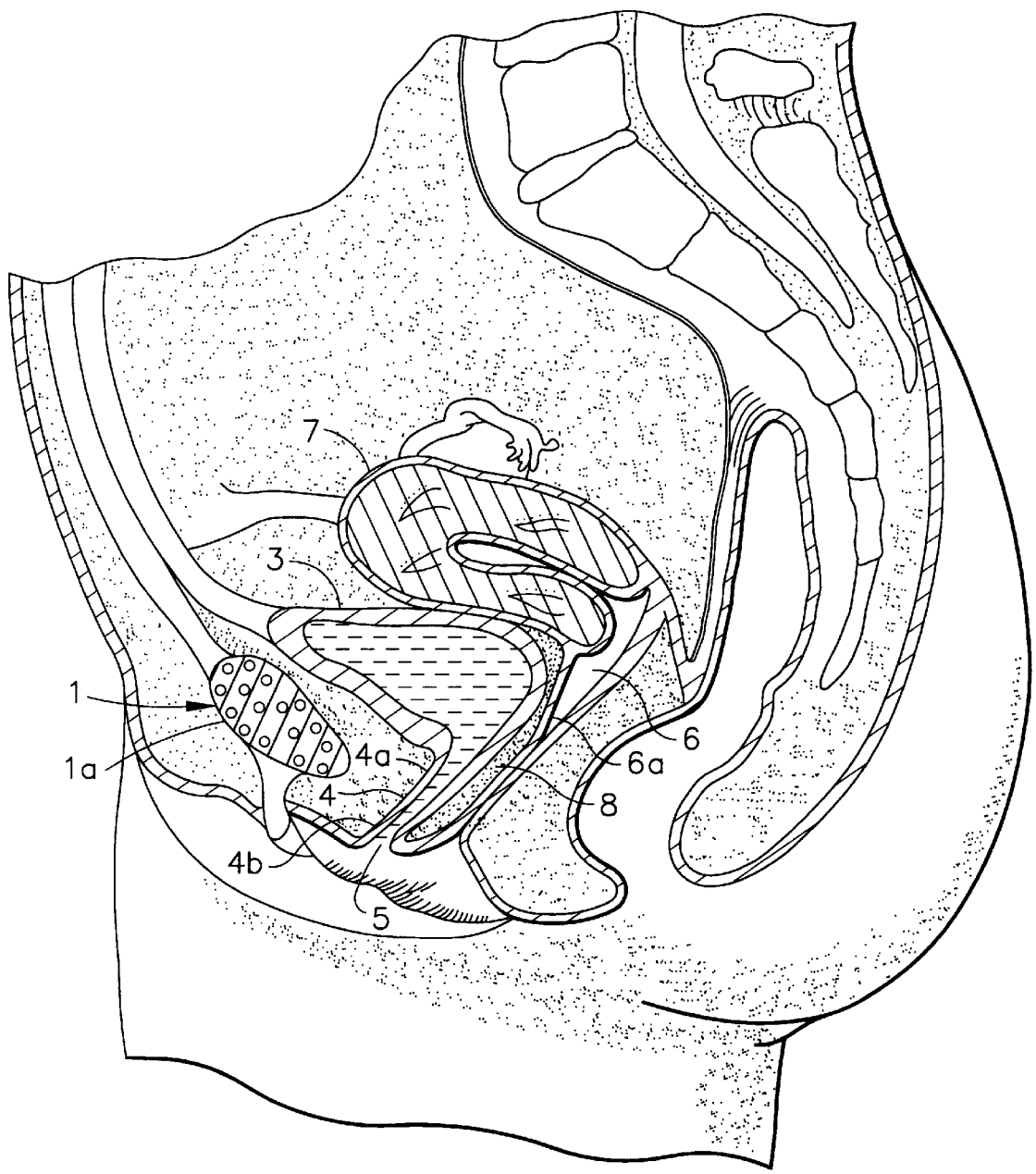
FIG. 3 is a fragmentary midsagittal cross-sectional view, similar to FIG. 1, and illustrating the prolapse of the urethra against the anterior wall of the vagina.

Throughout the drawings, like parts have been given like index numerals. Reference is first made to FIGS. 1 and 2.

These Figures illustrate the location of the urethra and bladder of a healthy, continent female.

The pelvis is generally indicated at 1 in FIGS. 1 and 2. The forward bony portions of the pelvis 1a and 1b (i.e. the pubic bone) are joined together by the pubic symphysis 2. The bladder 3 is located above and behind the pubic bone 1a and 1b. The urethra extends from the bladder 3 downwardly to the urinary meatus 5.

The vagina 6 is located behind the bladder and urethra and is surmounted by the uterus 7 which overlies the bladder.

The upper 20 percent of the urethra constitutes the urethra-vesical junction or bladder neck portion. The lowermost 20 percent of the urethra leads to the urinary meatus 5. The intermediate 60 percent of the urethra (shown between index numerals 4a and 4b), is provided with a sphincteric mechanism, and support of this part of the urethra is believed to be of key importance for continence. This is the part of the urethra which is subject to the greatest pressure as the result of prolapse.

Attention is again directed to FIG. 1, and particularly to FIG. 2. It has long been understood that female continence is largely a factor of the proper support and stabilization of the bladder 3 and urethra 4 in their normal retropubic state and particularly during coughing, straining and the like. In the healthy, continent female, the urethra and bladder are separated from the extraabdominal area by a hammock-like supportive layer comprising the web of endopelvic fascia 8 and the anterior vaginal wall 6a. As is most clearly shown in FIG. 2, the web of endopelvic fascia 8 is attached to the arcus tendineus fascia pelvis 9 at the right side of the pelvis (as viewed in FIG. 2) and to the arcus tendineus fascia pelvis 10 on the left side of the pelvis (as viewed in FIG. 2). The arcus tendineus fascia pelvis 9 extends from the ischial spine 11 to its insertion in the pubic bone portion 1a at 12. Similarly, the arcus tendineus fascia pelvis 10 extends from the ischial spine 13 to the insertion of the arcus tendineus fascia pelvis in the pelvic bone portion 1b, at 14.

The urethra 4 is additionally supported by a pair of pubourethral ligaments 15 and 16. Pubourethral ligament 15 is attached to the side of urethra 4 and extends forwardly to the pubic bone 1a adjacent the insertion 12 of the arcus tendineus fascia pelvis 9. In a similar fashion, the pubourethral ligament 16 extends from the opposite side of the urethra 4 to the pubic bone 1b adjacent the insertion 14 of the arcus tendineus fascia pelvis 10. The attachment of the pubourethral ligaments to the sides of urethra 4 are located at the above-noted intermediate 60 percent of the urethra.

From the above, it will be apparent that weakening of the endopelvic fascia 8, weakening of the anterior vaginal wall 6a, weakening of the attachments to the pubic bone and stretching of the pubourethral ligaments 15 and 16 can result in urethral hyper-mobility and incontinence. The sling of the present invention not only supports the normal urethral suspensistory mechanism, but also limits urethral descent at the site of continence control. Since the urethra cannot be elevated above the level of attachment of the sling to the inferior/posterior border of the pubis, it functions only with increasing intraabdominal pressure to prevent urethral descent.

Figure 4:
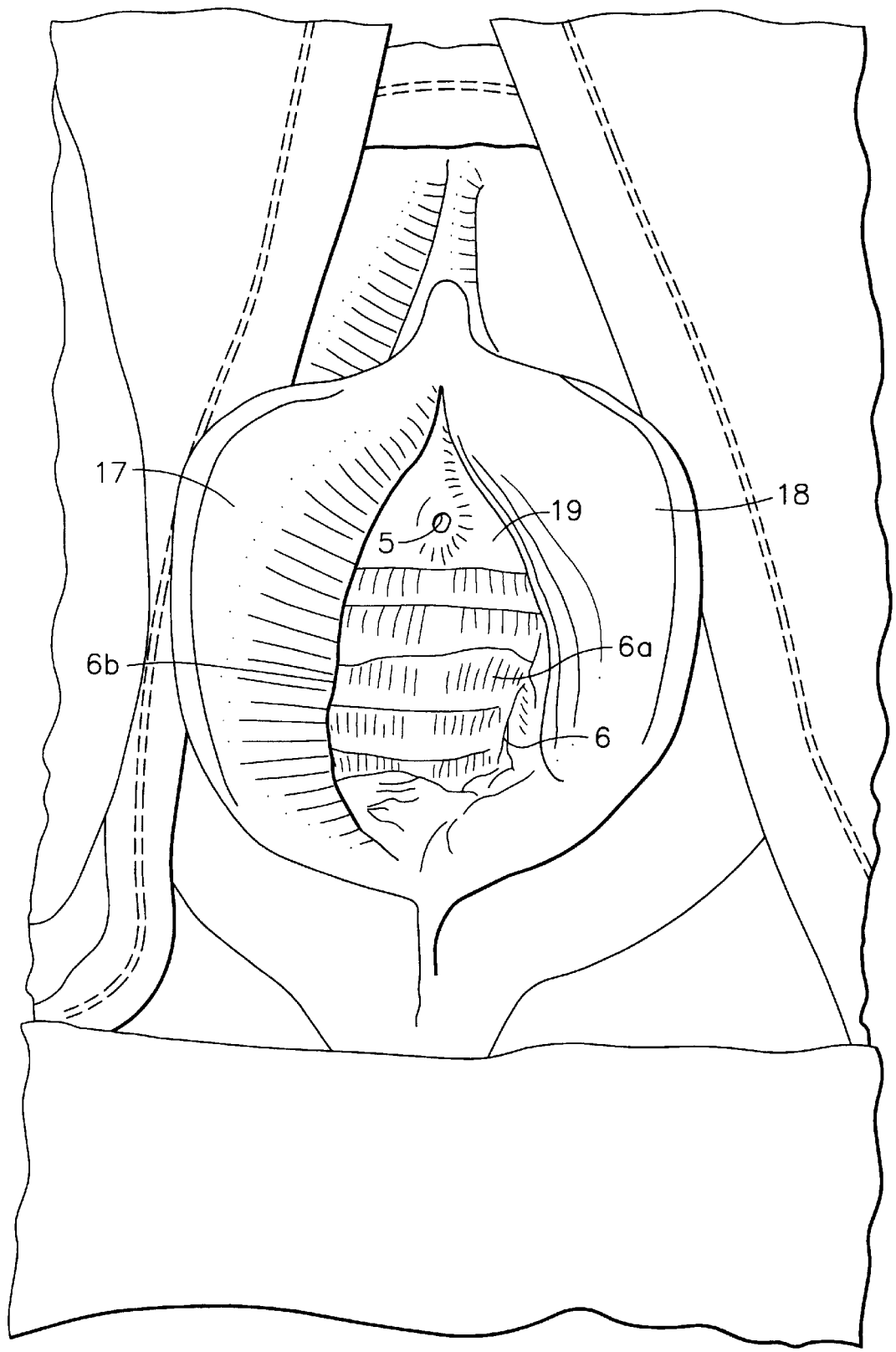
FIG. 4 is a frontal surgical view of the external female genitalia in surgical preparation with the labia minora in open position exposing the vestibule and the lower vagina of a female patient having the prolapse condition illustrated in FIG. 3.

At this point, the manner in which the system of the present invention is applied and used will now be described. Reference is first made to FIG. 4 which is a frontal or surgical view of the female genitalia with the labia minora 17 and 18 parted to reveal the urethral meatus 5 and the vestibule 19. The opening of the vagina 6 is shown at 6b. The anterior wall 6a of the vagina is also shown. Prolapse of the bladder, the urethra and the anterior wall 6 of the vagina is evidenced by a bulging of the vagina (as shown) and the fact that the anterior wall 6a falls away less steeply than would be the case in a healthy woman. Depending upon the severity of the prolapse, the anterior wall 6a of the vagina may extend through the vaginal opening 6b.

Figure 5:
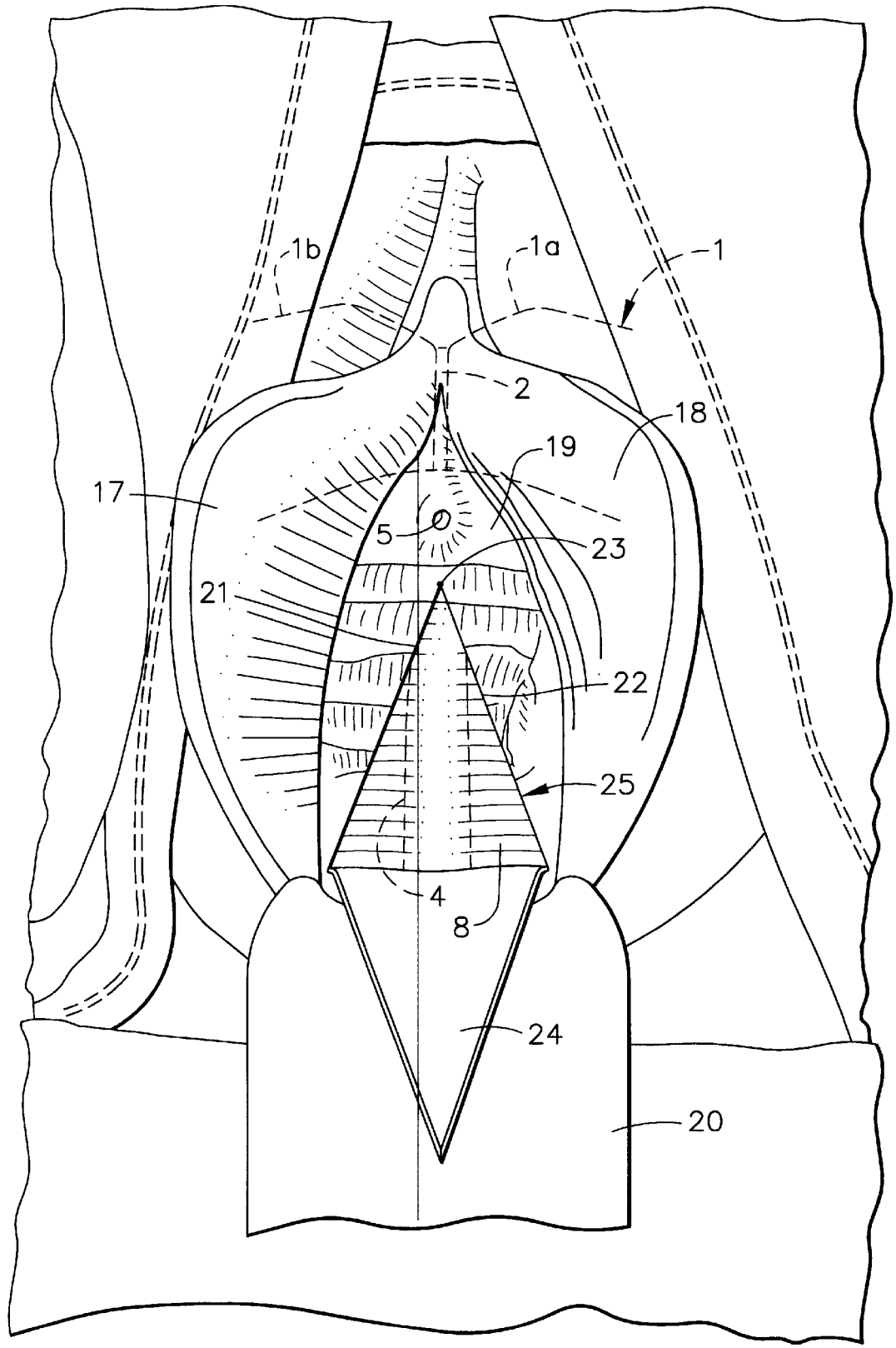
FIG. 5 is a fragmentary surgical view, similar to FIG. 4, and illustrates the posterior orifice of the vagina distended by means of a vaginal retractor, together with an incision made in the anterior wall of the vagina exposing the fascia tissue covering the urethra.

Reference is now made to FIG. 5. In this Figure the posterior wall of the vagina and the adjacent portion of the vaginal opening 6b are distended by means of a vaginal retractor 20. A pair of divergent incisions 21 and 22 is made, beginning at posterior urethral fold, indicated at 23. That portion 24 of the anterior vaginal wall 6 between the incisions 21 and 22 is carefully separated from the endopelvic fascia 8 forming a triangular flap 24. The vaginal wall flap 22 can be used as a tractor to pull the operative field into better view. With the flap 22 in the position shown, it will be noted that a triangular incision, generally indicated at 25, results.

While incisions of other configurations can be used, the above described triangular incision 25 has certain advantages. First of all, the vaginal wall edges may be trimmed of excess material having been stretched by prolapse. Furthermore, the endopelvic fascia has been left intact with minimal damage to the local nerve supply to the urethra and bladder, and with little damage to the blood supply of the endopelvic fascia.

Figure 6:
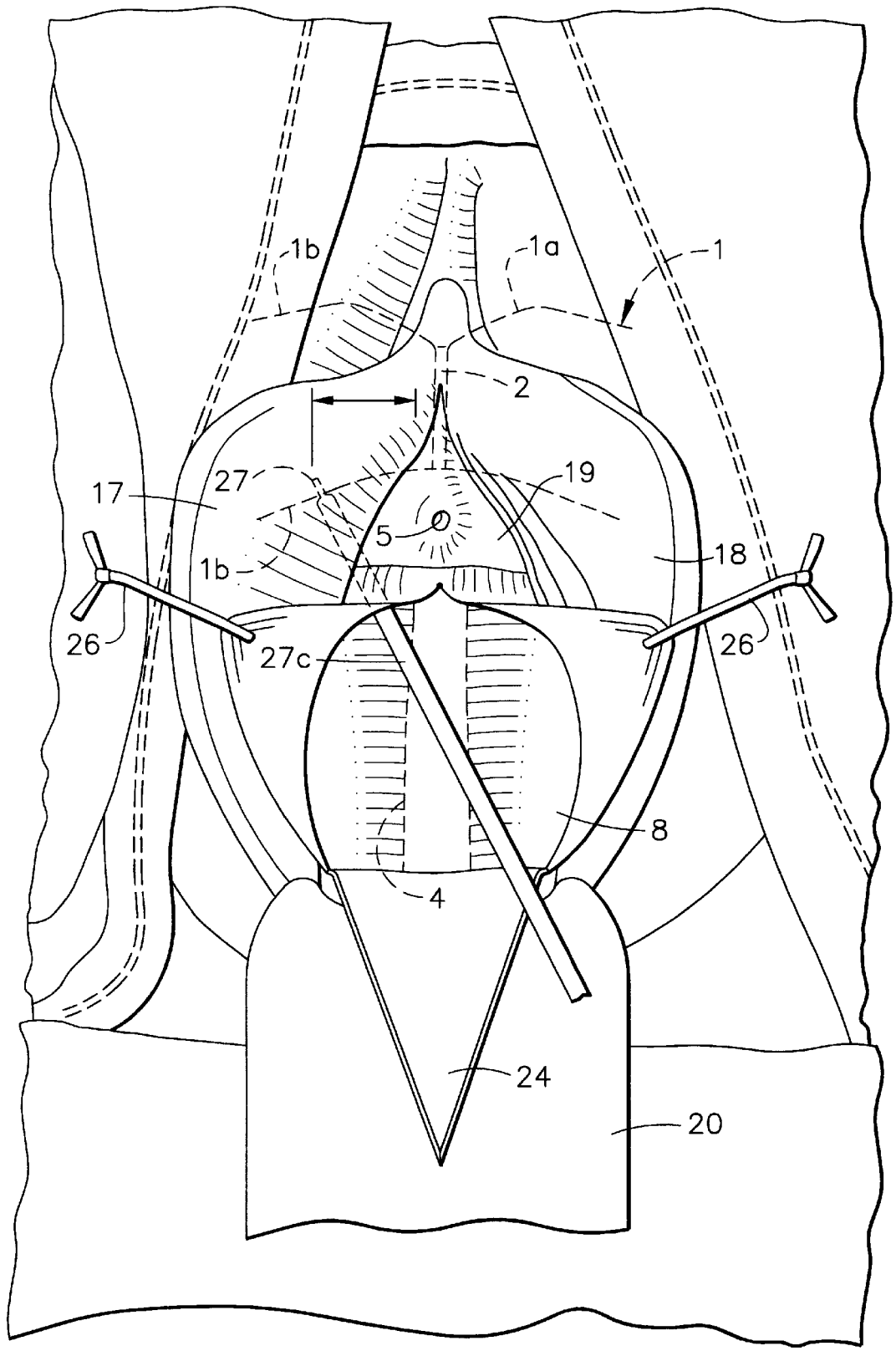
FIG. 6 is a fragmentary surgical view similar to FIG. 5 and illustrates the lateral edges of the incision stretched in open position and the placement of a suture-bearing anchor screw retropubically at the posterior/inferior border of the pubic bone to the left of the pubic symphysis and within 1 to 2 mm from the insertion of the arcus tendineus fascia pelvis.

The endopelvic fascia attachment to the vaginal epithelium having been separated, the incision 25 may be stretched to a more open position and held in that position by retractors, or temporary stitches engaging the adjacent drape, as shown at 26 in FIG. 6. At this point, dissection is carried out laterally to assess the integrity of the lateral attachment of the endopelvic fascia to each arcus tendineus fascia pelvis 9 and 10. Evaluation is made by palpation and direct visualization. Repairs by suturing may be made, if required. These sutures are left untied until the system of the present invention is in place. Additional repairs may also be made, if required. The system of the present invention can now be put in place. To this end, a pair of pubic bone anchor screws are located in the pubic bone portions 1a and 1b. In FIG. 6, an anchor screw 27 is shown being drilled in place in the pubic bone portion 1b. The site of the pubic bone anchor screw 27 is determined by palpating the course of the arcus 10 (see FIG. 2) from the ischial spine 13 to the arcus insertion 14 into the posterior/inferior aspect of pubic bone portion 1b. The anchor screw 27 is provided with a pair of sutures 27a and 27b affixed thereto. The anchor screw 27 and its sutures 27a and 27b are located within a driver 27c which, in turn, may be mounted in a surgical drill (not shown). A non-limiting example of such an anchor screw and driver is taught in U.S. Pat. No. 4,632,100. With respect to the sutures 27a and 27b, excellent results have been achieved with permanent 0 sutures manufactured by Ethicon, Inc. of Summerville, N.J. and sold under the registered trademark Mersilene®.

Figure 7:
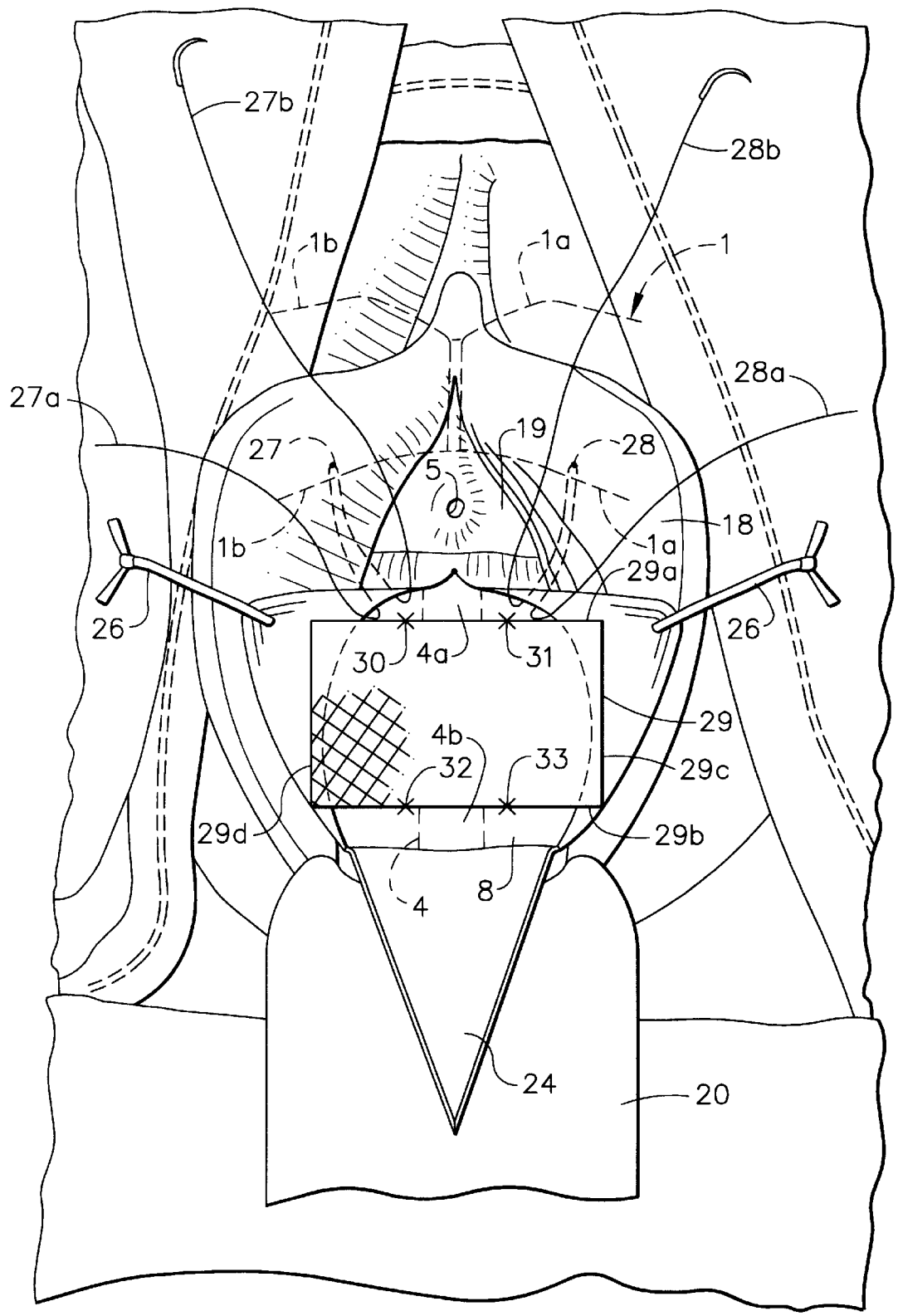
FIG. 7 is a fragmentary surgical view, similar to FIG. 6, and illustrates both suture-bearing anchor screws in place in the pubic bone and a rectangular piece of surgical mesh overlying the urethra and sutured adjacent either side of the urethra to the endopelvic fascia.

Anchor screw 27 is placed approximately one fingerbreadth laterally of the urethra 4 and approximately 1 cm laterally of the symphysis pubis 2. The anchor screw 27 is then directed to the retropubic area approximately 0.5 cm posteriorly and superiorly from the inferior edge of the ischial ramus. Once located, the anchor screw 27 is driven into the pubic bone and is set. The sutures 27a and 27b are temporarily laid aside as is shown in FIG. 7. It will be understood that a second anchor screw 28 will be attached to the pubic bone portion 1a in precisely the same manner and at the corresponding position on the pubic bone portion 1a. This is shown in FIG. 7. The anchor screw 28 is provided with a pair of sutures 28a and 28b which are laid aside as shown in FIG. 7.

A substantially rectangular patch 29 of surgical mesh, approximately 3 cm wide and 6 cm long is then provided. Excellent results have been achieved by using a surgical mesh manufactured by Ethicon, Inc. of Summerville, N.J. and sold under the registered trademark Mersilene®. The surgical mesh patch is shown in FIG. 7 at 29. The patch is provided with longitudinal edges 29a and 29b and transverse edges 29c and 29d. The mesh 29 is laid upon the endopelvic fascia 8 with its longitudinal edges 29a and 29b extending transversely of the urethra 4 beneath the endopelvic fascia 8. Four permanent sutures are used to transfix the mesh 29 along the lateral borders of the urethra at the edges 29a and 29b of mesh 29. These sutures are shown at 30, 31, 32 and 33 in FIG. 7. The sutures are so positioned as to allow a slight trough-like space between the mesh 29 and the endopelvic fascia 8 and urethra 4. This trough-like space prevents undue tension on the urethra by the mesh, when the mesh is formed into a sling, as will be apparent hereinafter. Excellent results were achieved when the sutures 30–33 constituted permanent 000 sutures manufactured by Ethicon, Inc. of Summerville, N.J. and sold under the registered trademark Ethibond®. It will further be noted in FIG. 7 that the mesh 29, from longitudinal edge 29a to longitudinal edge 29b extends along the above-described intermediate 60% of the length of the urethra 4, as indicated by the points 4a and 4b shown in FIG. 7.

Figure 8:
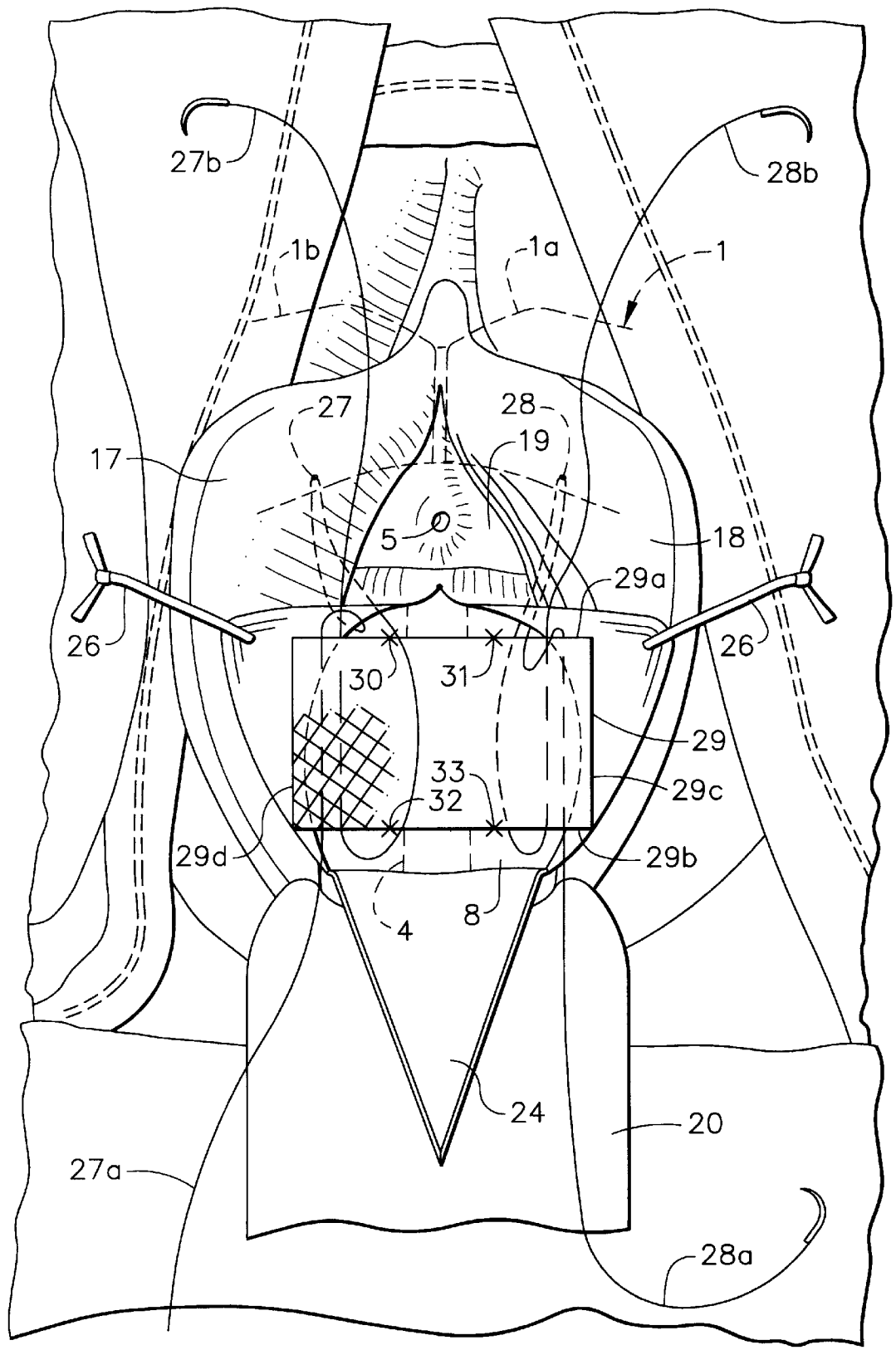
FIG. 8 is a fragmentary surgical view, similar to FIG. 7, and illustrates the sutures of each anchor screw oppositely threaded through its respective side of the mesh.
Figure 9:
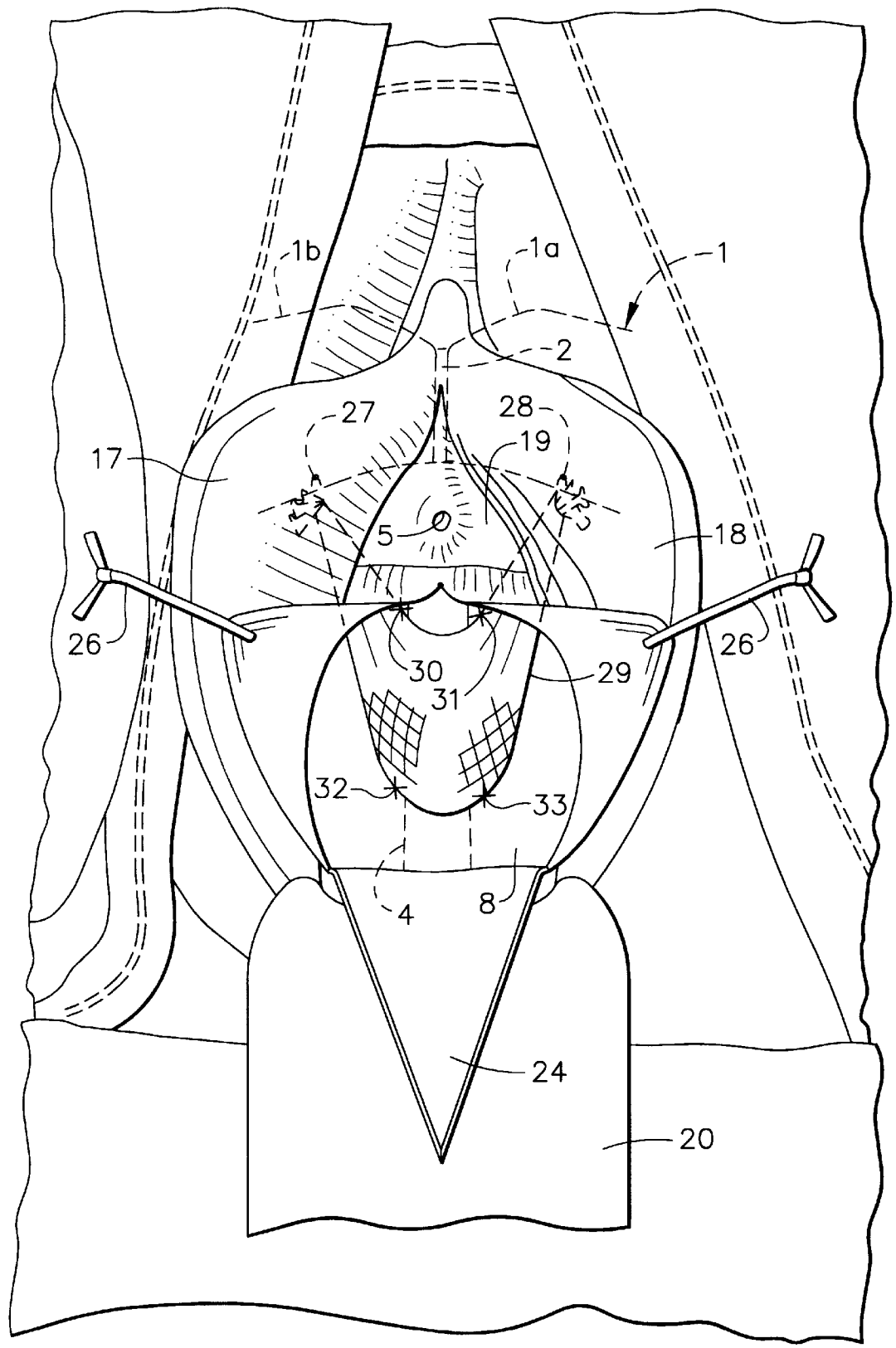
FIG. 9 is a fragmentary surgical view, similar to FIG. 8 and illustrates the anchor screw sutures being tensioned and tied, bringing the lateral edges of the mesh into conjunction with the anchor screws, forming a sling support for the urethra.
Figure 10:
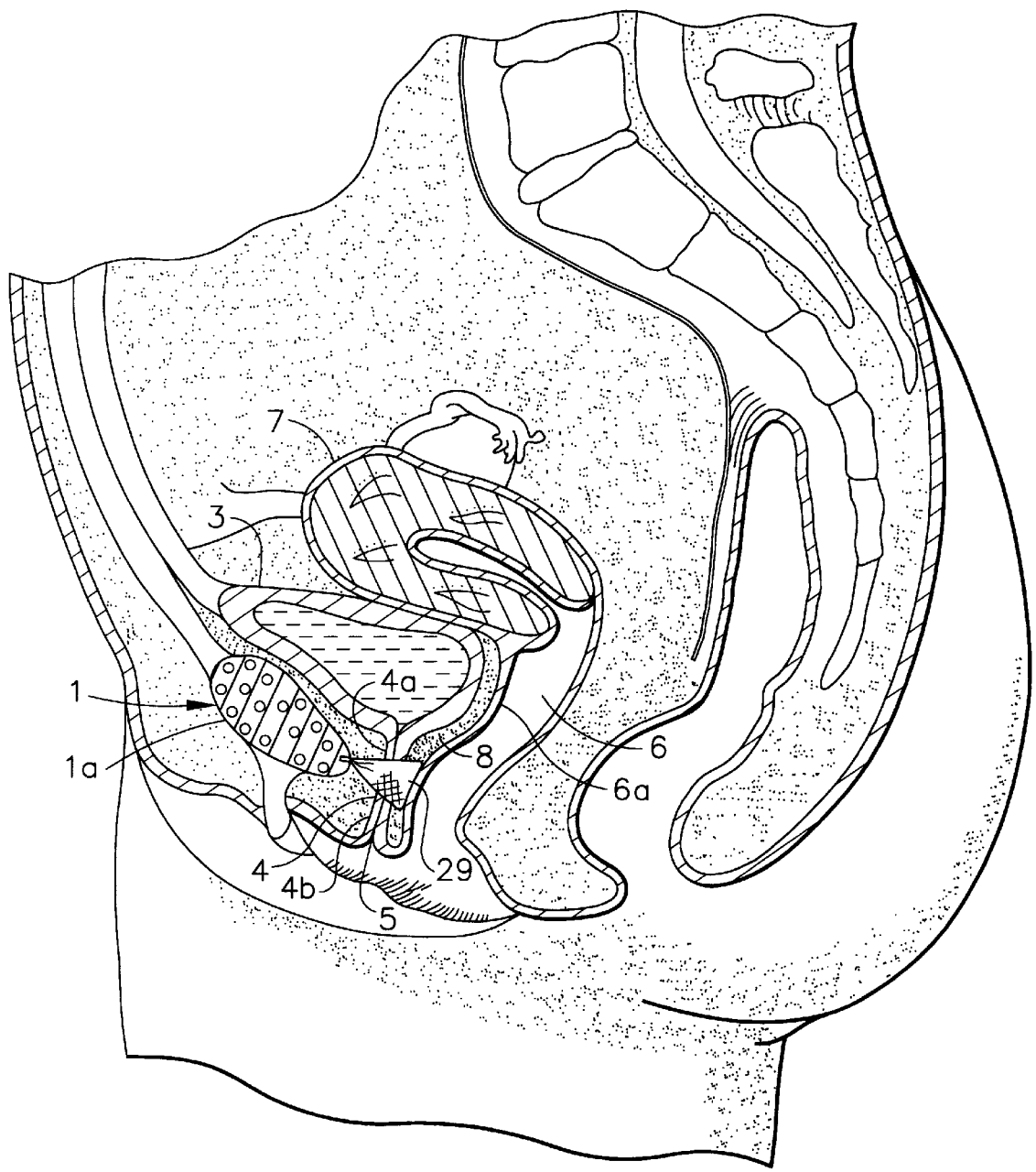
FIG. 10 is a fragmentary midsagittal cross-sectional view, similar to FIG. 1, and illustrates the urethra, bladder and neighboring organs of a woman whose urinary prolapse has been corrected by the system of the present invention.

Reference is now made to FIG. 8. In this Figure, it is shown that the permanent sutures 27a and 27b of anchor screw 27 are woven transversely of the mesh 29 in opposite directions between the longitudinal mesh edges 29a and 29b, and inset from the transverse mesh edge 29d. In a similar fashion, the sutures 28a and 28b are woven transversely of mesh 29 in opposite directions between the longitudinal edges 29a and 29b of the mesh, and inset from the transverse mesh edge 29c. The placement of the anchor sutures through the mesh is determined by placing upward tension on the mesh under cystoscopic guidance to determine the approximate tension required for urethral coaptation from each end of the mesh. As is shown in FIGS. 9 and 10, the sutures 27a and 27b and sutures 28a and 28b are tied in a bilateral fashion to their respective points of attachment to the pubic bone portions 1a and 1b. This causes the mesh 29 to be transformed into a sling.

Thereafter, the repair sutures for attaching the endopelvic fascia to the arcus tendineus fascia pelvis 9 and/or 10 are tied sequentially. Any mid-line or transverse defects are noted and repaired. Additional repairs may be made depending upon the requirement of the individual patient. Then, the triangular flap 24 is removed and the cut edges of the anterior vaginal wall are approximated with absorbable 00 polyglycolic sutures in a running fashion. At this point, the cul-de-sac and posterior vaginal segment defects are repaired. Cystoscopic examination of the urethra and the urethral orifices with indigo carmine dye are performed. Bladder drainage is provided by a suprapubic cystotomy.

Prior art incontinence procedures involving the use of a sling have enjoyed excellent surgical success rates. They have, on the other hand, been plagued with numerous drawbacks including voiding dysfunction, urinary retention, detrusor instability, infection, and erosion of the sling material. A number of these problems are, in all likelihood, related to difficulty in achieving the proper tension of the sling.

Figure 11:
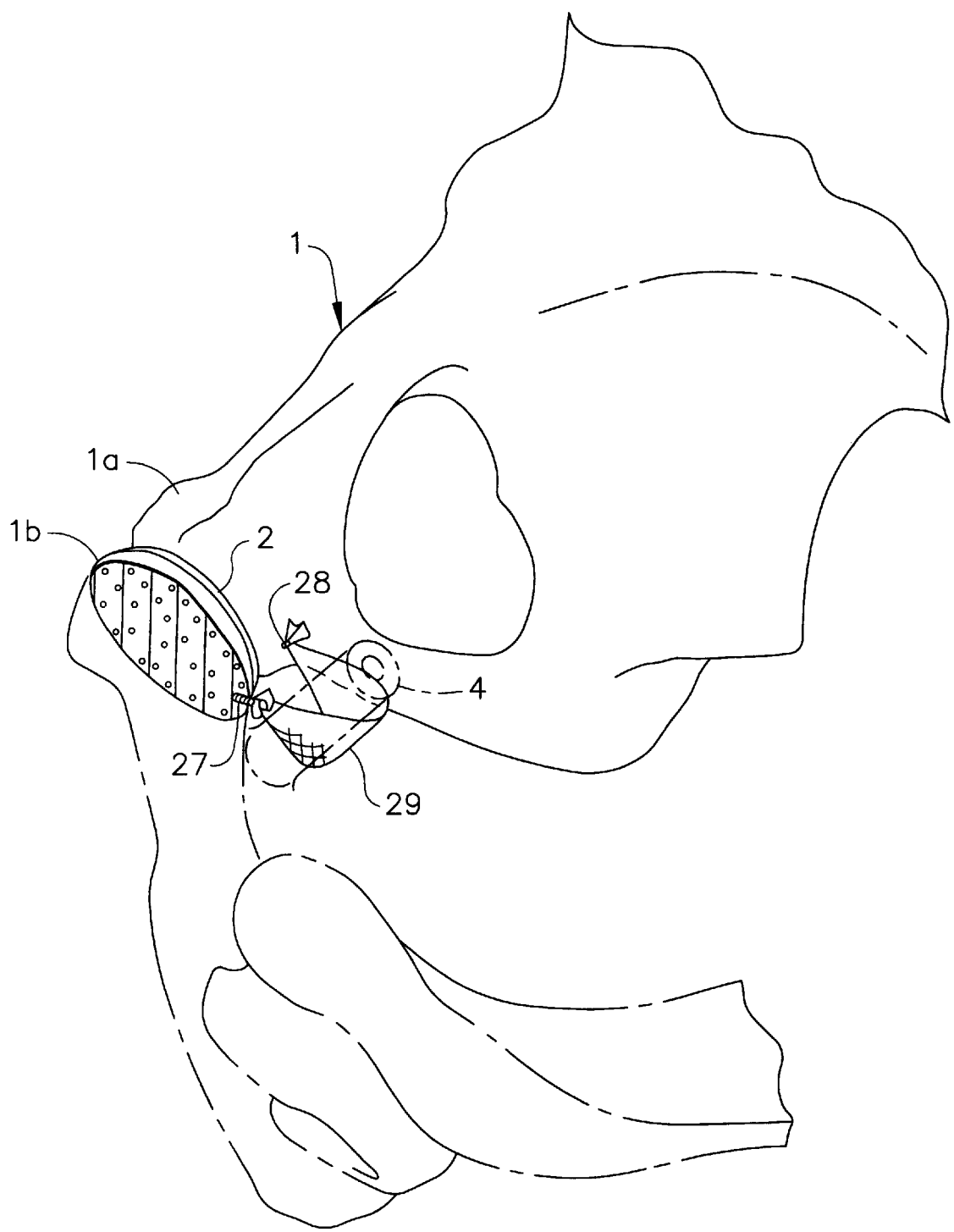
FIG. 11 is a fragmentary view of the pubic bone and the urethra, the urethra being supported by the system of the present invention.

The system of the present invention (i.e. the anchor screws 26 and 28 and their placement, the sutures 26a, 26b, 28a and 28b and the sling 29 and its placement) is characterized by a number of advantages (see FIG. 11). It is generally believed (as indicated above) that urethral hypermobility is caused by deficiencies in the arcus tendineus fascia pelvis and the pubourethral ligaments. In addition, the pubourethral ligaments are subject to stretching or elongation. None of these damaged, or elongated, or deficient muscular and fascial paraurethral tissues is used to supply the support and stabilization provided by the system of the present invention. The system of the present invention does not hyperelevate the urethra (see FIG. 10) by attachment to the superior border of the pubis, to Cooper's ligament or to the rectus abdominus fascia. It is to be noted that in the normal continent female, the urethral position is never found to be hyperelevated (see FIG. 1). By suturing the mesh sling of the present invention to anchor screws located, as described above, to either side of the symphysis pubis in the retropubic area posteriorly and at about 0.5 cm superiorly of the inferior edge of the ischial ramus, such hyperelevation is precluded. The sutures that connect the mesh sling to the anchor screws are, themselves, short which not only assists in developing the proper tension, but also minimizes lateral movement cause by intraabdominal pressure. Such movement is characteristic of long length sutures. In addition, it will be noted that the sling of the present invention differs from the pubourethral ligaments primarily in that the sling passes about and behind the urethra, rather than being attached to the urethra sides. However, sutures 30 through 33 simulate an attachment to the urethra sides. Those portions of the sling between each anchor and its respective pair of sutures 30–32 and 31–33 bear most of the support load and closely simulate the pubourethral ligaments. As a result of this, the sling not only serves much the same purpose as the pubourethral ligaments, but also serves much the same purpose as the endopelvic fascia and the anterior vaginal wall in a healthy woman. The sling engages the urethra and stabilizes it by passing about the above-described intermediate 60 percent of the urethra, believed to be the primary continence control portion of the urethra. It has been found that repair of other site-specific defects of genital prolapse corrects only those defects and does not alter the incontinence mechanism. For example, paravaginal repairs of the endopelvic fascia from one arcus to the other can only be expected to correct the protrusion causing a cystourethrocele. If the pubourethral ligaments are damaged, their ability to limit urethral descent with increasing intraabdominal pressures will remain impaired no matter how tight the endopelvic fascia is stretched from one arcus to the other.

Finally, the procedure of the present invention is a relatively simple one and, as indicated above, proper tension on the sling is far easier to determine than in prior art procedures.

The present invention has been described in the terms of vaginal installation of the system of the present invention. At this time, this is the preferred procedure. Nevertheless, it will be understood that the system of the present invention could be installed abdominally or laproscopically.

Figure 12:
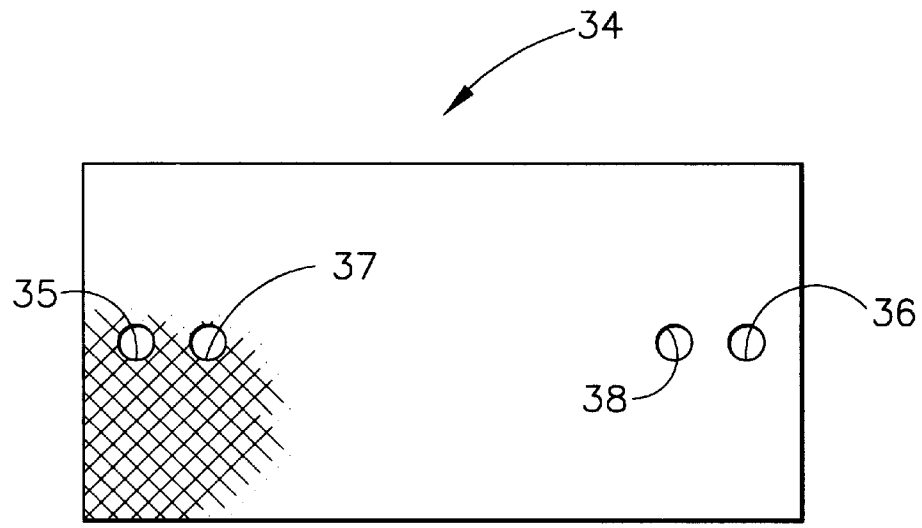
FIG. 12 is an elevational view of another embodiment of a surgical mesh sling.

Reference is now made to FIG. 12 which illustrates another embodiment of the surgical mesh member which serves as a urethral sling. The mesh member is generally indicated at 34 and preferably is made of the same material described with respect to the surgical mesh member 29 of FIG. 7. The surgical mesh member 34 is provided with a pair of holes 35 and 36. The holes 35 and 36 are sized to just nicely receive the shanks of headed surgical anchor screws.

The procedure for installing the surgical mesh member 34 is substantially identical to that described with respect to surgical mesh member 29, with the exception that surgical mesh member 34 is not tied to anchors by sutures. Surgical mesh member 34 is provided with four permanent sutures equivalent to sutures 30–33 of FIG. 7 whereby it is attached to the endopelvic fascia 8. Again, the sutures are so positioned as to allow a slight trough-like space between the mesh 34 and the endopelvic fascia 8 and urethra 4. As indicated with respect to sutures 30–33 of FIG. 7, this trough-like space prevents undue tension on the urethra by the mesh, when the mesh is formed into a sling.

An anchor screw (not shown) is caused to have its shank inserted through hole 35 in mesh member 34 and is located in the posterior/inferior aspect of the pubic bone portion 1a. The site of the anchor screw is determined in exactly the same manner as that described with respect to anchor screw 27 of FIG. 7. In a similar fashion, the shank of a second headed anchor screw is passed through the hole 36 in mesh member 34 and is located in the posterior/inferior aspect of pubic bone portion 1b.

Preferably, mesh member 34 is provided with more than one pair of holes. In this way, the surgeon can select an appropriate pair of holes to achieve the best placement of the gauze member sling 34 when it is attached to the posterior/inferior aspect of the pubic bone portions 1a and 1b. To this end, mesh member 34 is shown having a second pair of holes 37 and 38.

Preferably, the holes 35–38 are provided with reinforced stitching about their edges in a manner somewhat similar to button holes.

Figure 13:
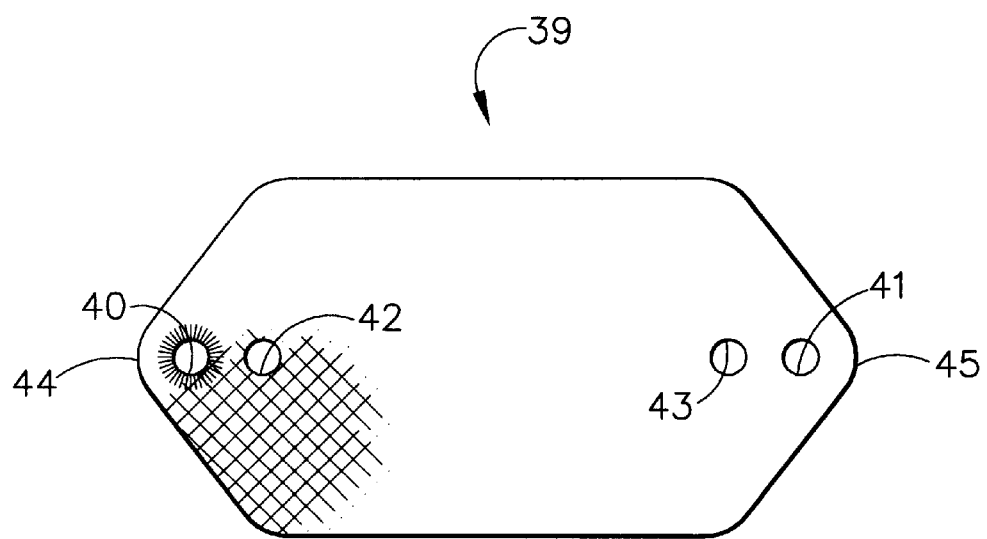
FIG. 13 is an elevational view of yet another embodiment of a surgical mesh sling.

It is within the scope of the invention to shape the ends of the mesh member. This is illustrated in FIG. 13 wherein the mesh member 39, having a first pair of holes 40–41 and a second pair of holes 42–43, is provided with somewhat pointed ends 44 and 45. It will be understood that the ends may be otherwise shaped. For example, they could be arcuate or rounded.

The mesh sling elements 34 and 39 of FIGS. 12 and 13 tend to simplify the surgical procedure since it is no longer necessary to weave pairs of sutures transversely of the mesh member ends as shown in FIG. 8, and to tie these sutures as shown in FIG. 9. The number of pairs of holes in the mesh elements 34 and 39 does not constitute a limitation of the present invention. Excellent results can be achieved using gauze elements 34 or 39 having a length of about 6 centimeters and a width of about 3 centimeters.

As used herein and in the claims such works as "uppermost", "lowermost", "right", "left", and the like are used in conjunction with the drawings for clarity.

Modifications may be made in the invention without departing from the spirit of it. For example, throughout the specification, the surgical sling of the present invention has been described as a mesh sling. It will be understood by one skilled in the art that the sling could also be made of autologous fascia or cadaveric fascia.

Furthermore, while the system and method of the present invention are described in their application to women, they could also be applied to men, as well.

What is claimed:

1. A pubic bone-mounted urethra stabilization and support system for the long term cure of recurrent female urinary incontinence, said system comprising a pair of anchors adapted to be affixed to the posterior/inferior pubic bone to either side of the symphysis pubis, a surgical sling means adapted to be passed behind and about the urethra and the endopelvic fascia therebehind, for replacing damaged pubourethral ligaments and for supporting the urethra in its normal anatomic retropubic position said surgical sling means having spaced lateral end portions, each of said anchors operatively engaging one of said sling end portions, and adjustment means to position said surgical sling means relative to said anchors for restoring, supporting and stabilizing functional urethral continence anatomy and to prevent urethral descent under intraabdominal pressure.

2. The structure claimed in claim 1 wherein said surgical sling means also has upper and lower longitudinal edges, said sling end portions terminating in end edges.

3. The structure claimed in claim 2 including a pair of sutures connected to the upper and lower edges of said surgical sling means and adapted to extend on one side of the urethra for attachment to the endopelvic fascia and a similar pair of sutures connected to the upper and lower edges of said surgical sling means and adapted to extend on the other side of urethra for attachment to said endopelvic fascia.

4. The structure claimed in claim 3 wherein said pairs of sutures to either side of the urethra are so located as to form therebetween a trough-like configuration in said surgical sling means to prevent undue tension on the urethra by said surgical sling means when tied to said anchors.

5. The structure claimed in claim 1 wherein said surgical sling means has a trough-like configuration to prevent undue tension on the urethra.

6. The structure claimed in claim 5 wherein said surgical sling means is made from surgical mesh.

7. The structure claimed in claim 6 including a pair of permanent sutures affixed to each of said anchors, the anchor sutures of each pair being woven in opposite directions transversely through one of said surgical sling means end portions, said anchor sutures comprising said adjustment means.

8. The structure claimed in claim 7, including a pair of sutures to one side of the urethra attaching said upper and lower edges of said surgical sling means to the endopelvic fascia and a similar pair of sutures to the other side of the urethra attaching said upper and lower edges of said surgical sling means to the endopelvic fascia.

9. The structure claimed in claim 8, wherein the pairs of sutures to either side of the urethra are so located as to form therebetween a trough-like configuration in said surgical sling means to prevent undue tension on said urethra by said sling when tied to said anchors.

10. The structure claimed in claim 9 wherein said surgical sling means upper and lower edges are about 6 cm long, said sling end portions having end edges about 3 cm long.

11. The structure claimed in claim 2 wherein said end edges are formed other than rectilinear.

12. The structure claimed in claim 2 wherein said end portions of said surgical sling means each have at least one hole therethrough said anchors comprising anchor screws each having a shank and a head, said holes being sized to just nicely receive said anchor screw shanks.

13. The structure claimed in claim 2 wherein each of said end portions has at least two holes therethrough, locating said holes in each sling end portion in side-by-side relationship and longitudinally of said sling, said holes comprising said adjustment means.

14. The structure claimed in claim 13 including reinforcing stitching about the periphery of said holes.

15. The structure claimed in claim 1 wherein said surgical sling means is sufficiently dimensioned, configured and constructed relative to the urethra so as to be adapted to be passed behind and about the intermediate 60% portion of the urethra from the lower 20% portion to the upper 20% portion of the urethra.

16. The structure claimed in claim 1 including a pair of permanent sutures affixed to each of said anchors, the anchor sutures of each pair being woven in opposite directions transversely through one of said surgical sling end portions, said anchor sutures comprising said adjustment means.

17. The structure claimed in claim 1 wherein said surgical sling means comprises a rectangular piece of mesh about 6 cm long and about 3 cm wide.

18. The structure claimed in claim 1 wherein said anchors comprise anchor screws each of which extend through a hole in one of the sling end portions, said anchors screws when extending through said holes comprising said adjustment means.

19. A method of providing a long term cure for recurrent female urinary incontinence comprising the step of first making an incision in a vaginal wall through which the following additional steps are performed including mounting a pair of anchors in the posterior/inferior pubic bone to either side of the symphysis pubis, providing a surgical sling, locating said sling behind and about the urethra and the endopelvic fascia therebehind, said sling having lateral end portions, causing each of said anchors to operatively engage one of said sling end portions, and positioning said sling relative to said anchors to restore, support and stabilize functional urethral continence anatomy and to prevent urethral descent under intraabdominal pressure.

20. The method claimed in claim 19, including the step of making said sling of a piece of surgical mesh having upper and lower longitudinal edges, said end portions terminating in end edges.

21. The method claimed in claim 18 wherein said sling upper and lower edges are formed about 6 cm long and said sling end edges are formed about 3 cm long.

22. The method claimed in claim 20 including a pair of permanent sutures affixed to each of said anchors, weaving the sutures of each pair in opposite directions transversely through one of said surgical mesh sling end portions and tying said sutures to affix said sling end portions to their respective anchors.

23. The method claimed in claim 20 including the steps of providing at least one pair of holes, locating one hole of said pair in each end portion of said sling, providing a pair of headed anchor screws, sizing said holes to just nicely receive the shanks of said anchor screws, inserting the shanks of said anchor screws through said holes and affixing said anchor screws and thus said sling to the posterior/interior pubic bone to either side of the symphysis pubis.

24. The method claimed in claim 23, including the steps of providing at least two pairs of said holes, locating one hole from each pair in each of said sling end portions, and locating said holes in each sling end portion in side-by-side relationship longitudinally of said sling to facilitate adjustment.

25. The method claimed in claim 24, including the step of providing reinforcing stitching about the periphery of said holes.

26. The method claimed in claim 19 including the step of locating said sling behind and about the intermediate 60% portion of the urethra from the lower 10% portion to the upper 20% portion of the urethra.

27. The method claimed in claim 1 including the step of locating said anchors about 1 cm laterally of the symphysis pubis and about 0.5 cm posteriorly and superiorly of the inferior edge of the ischial ramus of the pubic bone.

28. The method claimed in claim 19 including the step of forming a trough-like configuration in the sling to prevent undue tension on the urethra.

29. The method claimed in claim 27, including the step of locating said sling behind and about the intermediate 60% portion of the urethra from the lower 10% portion to the upper 20% portion of the urethra.

30. The method claimed in claim 29, including the steps of attaching said sling at the upper and lower edges thereof to the endopelvic fascia at either side of the urethra by a pair of sutures at either side of the urethra.

31. The method claimed in claim 30, including the step of locating said pairs of sutures to either side of the urethra joining said upper and lower longitudinal edges of said sling to the endopelvic fascia in a manner forming therebetween a trough-like configuration in said sling to prevent due tension on the urethra by said sling.

32. The method claimed in claim 20, including the steps of attaching said sling at the upper and lower edges thereof to the endopelvic fascia at either side of the urethra by a pair of sutures at either side of said urethra.

33. The method claimed in claim 21 including the step of locating said pairs of sutures to either side of the urethra joining said upper and lower longitudinal edges of said sling to the endopelvic fascia in a manner forming therebetween a trough-like configuration in said sling to prevent undue tension on the urethra by said sling.

34. The method claimed in claim 19 wherein said incision in the vaginal wall is triangular shaped.

* * * * *

UNITED STATES PATENT AND TRADEMARK OFFICE
CERTIFICATE OF CORRECTION

PATENT NO. : 6,039,686
DATED : March 21, 2000
INVENTOR(S) : S. Robert Kovac

It is certified that error appears in the above-identified patent and that said Letters Patent is hereby corrected as shown below:

Column 11, line 31, claim 21, delete the numeral "18" and insert therefor the numeral --19--.
Column 12, line 14, claim 27, delete the numeral "1" and insert therefor the numeral --19--.

Signed and Sealed this

Sixth Day of February, 2001

*Attest:*

Q. TODD DICKINSON

*Attesting Officer*  *Director of Patents and Trademarks*